US00PP16584P2

(12) United States Plant Patent
Olesen

(10) Patent No.: US PP16,584 P2
(45) Date of Patent: May 30, 2006

(54) CLIMBING ROSE PLANT NAMED 'POULCY011'

(50) Latin Name: ***Rosa* hybrid**
Varietal Denomination: Poulcy011

(75) Inventor: Mogens Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 121 days.

(21) Appl. No.: 11/002,346

(22) Filed: Dec. 1, 2004

(51) Int. Cl.
*A01H 5/00* (2006.01)

(52) U.S. Cl. ..... Plt./114
(58) Field of Classification Search ..... Plt./114
See application file for complete search history.

*Primary Examiner*—Anne Marie Grunberg
*Assistant Examiner*—June Hwu

(57) ABSTRACT

A new garden rose plant of the climbing rose class which has abundant, pink flowers and attractive foliage. This new and distinct variety has shown to be uniform and stable in the resulting generations from asexual propagation.

2 Drawing Sheets

Botanical classification: *Rosa* hybrid.
Variety denomination: 'Poulcy011'.

SUMMARY OF THE INVENTION

The present invention constitutes a new and distinct variety of garden rose plant that originated from a controlled crossing between the female seed parent, an unnamed seedling, and the male pollen parent, 'Pouldiram', a rose variety by the same inventors, described and illustrated in U.S. Plant Pat. No. 12,568 issued Apr. 23, 2002.

The two parents were crossed during the summer of 1994 and the resulting seeds were planted in a controlled environment in Fredensborg, Denmark. The new variety is named 'Poulcy011'.

The new variety may be distinguished from its female seed parent by the following combination of characteristics:

1. The seed parent has an upright bushy growth habit, while 'Poulcy011' has a climbing growth habit.
2. 'Poulcy011' has more flower petals than the seed parent plant.
3. The seed parent has red flowers while 'Poulcy011' has pink flowers.

The new variety may be distinguished from its male pollen parent, 'Pouldiram', by the following combination of characteristics:

1. 'Pouldiram', has white flowers while 'Poulcy011' has pink flowers.
2. 'Pouldiram', has an upright and bushy growth habit, while 'Poulcy011' has a climbing growth habit.
3. 'Pouldiram' has fewer flower petals than 'Poulcy011'.

The objective of the hybridization of this rose variety was to create a new and distinct variety for garden use with unique qualities, such as:

1. Uniform and abundant medium pink flowers;
2. Vigorous, but compact growth when propagated both as a budded rose and on its own roots.
3. Disease resistance;
4. Reduced apical dominance in flowering habit. The new variety consistently produces flowers evenly from the lower branches to the top of the plant.

This combination of qualities is not present in previously available commercial cultivars of this type, known to the inventors, and distinguish 'Poulcy011' from all other varieties of which we are aware.

As part of the rose development program, Mogens N. Olesen germinated the seeds from the aforementioned hybridization during winter of 1995 and conducted evaluations on the resulting seedlings in a controlled environment in Fredensborg, Denmark.

'Poulcy011' was selected in the spring of 1996 by the inventors as a single plant from the progeny of the aforementioned hybridization.

Asexual reproduction of 'Poulcy011' by traditional budding and rooted cuttings was first done by Mogens N. Olesen in the nursery in Fredensborg, Denmark in July, 1996. This initial and other subsequent asexual propagations conducted in controlled environments have demonstrated that the characteristics of 'Poulcy011' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems, of 'Poulcy011'. Specifically illustrated in the drawings:

FIG. 1.1; Stem showing open flowers, branching, and the attachment of leaves, buds, and peduncles;

FIG. 1.2; Open flower;

FIG. 1.3; Flower buds upon opening;

FIG. 2.1; Petals detached;

FIG. 2.2; Sepals, receptacle, and pedicel;

FIG. 2.3; Mature and Juvenile stems exhibiting thorns;

FIG. 2.4; Mature leaves.

DETAILED DESCRIPTION OF THE VARIETY

The following is a description of 'Poulcy011', as observed in its growth in in a field nursery in Jackson County, Oreg. Observed plants are 2 years of age, and were grown on *Rosa multiflora* understock. Color references are made using The Royal Horticultural Society (London, England) Colour Chart, 1995, except where common terms of color are used.

For a comparison, several physical characteristics of the rose variety 'Poulvam', a rose variety from the same inventors described and illustrated in U.S. Plant patent application Ser. No. 10/269,793 dated Oct. 10, 2002, are compared to 'Poulcy011' in Chart 1.

CHART 1

| | 'Poulcy011' | 'Poulvam' |
|---|---|---|
| General tonality. | Red-Purple Group 62C and 62D with intonations of Red-Purple Group 58C at the center. | Red-Purple Group 62A. |
| Flower bud length, upon opening. | 17 mm. | 25 mm. |
| Fragrance. | Very light floral. | None. |

FLOWER AND FLOWER BUD

Blooming habit: Recurrent.

Flower bud:

*Size.*—Upon opening, 17 mm in length from base of receptacle to end of bud. Bud diameter is 10 mm.

*Bud form.*—Urceolate.

*Bud color.*—As sepals unfold, petals are distinctly Orange-Red Group 35B and Red Group 46A.

*Sepal inner surface.*—Color: Yellow-Green Group 144D with anthocyanic intonations of Greyed-Purple Group 184A. Surface: Strongly pubescent.

*Sepal outer surface.*—Color: Yellow-Green Group 144A with anthocyanic pigments of Greyed-Purple Group 183A. Texture: Smooth.

*Sepal shape.*—Apex: Cirrhose. Base: Flat an union with receptacle.

*Sepal margin.*—Many stipitate glands observed. Margins have strong foliaceous appendages on three of the five sepals.

*Sepal size.*—23 mm (l) by 6 mm (w).

*Receptacle.*—Texture: Smooth. Shape: Funnel shaped. Size: 3 mm (l)×4 mm (w). Color: Yellow-Green Group 144B. Anthocyanic pigments the color of Greyed-Purple Group 184B observed.

*Pedicel.*—Surface: Smooth. Stipitate glands produce strong fragrance when touched. Length: 22 to 25 mm. Diameter: 2.5 mm. Color: Yellow-Green Group 144B with anthocyanic pigments Greyed-Purple 184B. Strength: Somewhat strong.

Flower bud development: Flower buds are borne in clusters of 5 to 9 flower buds per stem. Inflorescence type is panicle. Reduced apical dominance in flower habit causes flower buds develop evenly from the base of the plant to the upper branches.

Flower bloom:

*Fragrance.*—Very light floral.

*Duration.*—The blooms have a duration on the plant of 10 days. Petals fall cleanly away from plant after flowers mature.

*Size.*—Flower diameter is 45 to 55 mm when open. Flower depth is 25 mm on average.

*Flower shape.*—Flowers are somewhat globular upon opening. After opening, petals form a rosette with petals of different sizes.

*Shape of flower, side view.*—Upon opening, Upper portion: Flat. Lower portion: Concave. After opening, Upper portion: Flat. Lower portion: Concave.

Petalage: Under normal conditions, flowers have 60 petals total, 7 to 10 of which are petaloids.

Petal color:

*Upon opening, outer petals.*—Upper surface: Red-Purple Group 68D. Lower surface: Red-Purple Group 62D with overlay of Red-Purple Group 62A.

*Upon opening, inner petals.*—Upper surface: Red-Purple Group 68D. Lower surface: Red-Purple Group 62D with overlay of Red-Purple Group 62A.

*Basal petal spots, upon opening.*—Upper surface: Yellow Group 4B. Lower surface: Yellow Group 4C.

*After opening, outer petals.*—Upper surface: Red-Purple Group 68D. Lower surface: Red-Purple Group 62D with overlay of Red-Purple Group 62A.

*After opening, inner petals.*—Upper surface: Red-Purple Group 68D. Lower surface: Red-Purple Group 62D with overlay of Red-Purple Group 62A.

*Basal petal spots, after opening.*—Upper surface: Yellow Group 4B. Lower surface: Yellow Group 4C.

General tonality: On open flower Red-Purple Group 62C to 62D with intonations of Red-Purple Group 58C at the center. No change in tonality at the end of the $10^{th}$ day.

Petals:

*Petal reflex.*—Somewhat reflexed at the margins. Overall petals are concavely shaped.

*Margin.*—Medium undulations of margin observed.

*Shape.*—Narrow elliptical in shape. Apex: Rounded. Base: Acute.

*Size.*—20 to 30 mm (l)×13 to 28 mm (w).

*Texture.*—Smooth.

*Thickness.*—Average.

Petaloids:

*Quantity.*—7 to 10.

*Shape.*—Elliptical.

*Color.*—Upper surface: Red-Purple Group 68D. Lower surface: Red-Purple Group 62D with overlay of Red-Purple Group 62A.

*Size.*—15 mm (l)×8 mm (w).

Reproductive organs:

*Pollen.*—None observed.

*Anthers.*—Size: 2.5 mm in length. Color: Orange Group 24B. Quantity: 10 to 15 on average.

*Filaments.*—Color: Yellow-Green Group 145C. Length: 4 mm.

*Pistils.*—Length: 8 mm. Quantity: 60 on average.

*Stigmas.*—Superior in location relative to the length of the filaments and the height of the anthers. Color: Orange-White Group 158B.

*Styles.*—Color: Yellow-Green Group 149D with intonations of Red-Purple Group 58C and 58D.

*Hips.*—None Observed in the field nursery in Jackson County Oreg.

PLANT

Plant growth: When grown as a budded field grown plant on *Rosa multiflora* understock, the average height of the plant is 150 to 200 cm. Average spread is 100 cm.

Stems:

*Color.*—Juvenile growth: Greyed-Purple Group 183B with intonations of Yellow-Green Group 144B. Mature growth: Yellow-Green Group 144B with Greyed-Orange 174A.

*Length.*—On average, canes are 100 cm from the base of the plant to the flowering portion.

*Diameter.*—8 mm.

*Internodes.*—On mature canes, there is an average distance of 45 mm between nodes.

*Surface texture.*—Young wood: Smooth. Older wood: Smooth.

Thorns:

*Incidence.*—6 thorns per 10 cm of stem.

*Length.*—15 mm.

*Shape.*—Upper side: Concave. Lower side: Concave.

*Juvenile thorns.*—Color: Greyed-Purple Group 183A.

*Mature thorns.*—Color: Greyed-Yellow Group 162B with intonations of Greyed-Orange Group 166A.

Plant foliage: Normal number of leaflets leaves in middle of the stem: 5 to 7 leaflets.

*Compound leaf.*—110 mm (l)×65 mm (w).

*Quantity.*—2 leaves per 10 cm of stem on average.

*Color of mature foliage.*—Upper side: Yellow-Green Group 147A. Lower side: Yellow-Green Group 146B.

*Color of juvenile foliage.*—Upper side: Yellow-Green Group 146C with anthocyanic intonations of Greyed-Purple 183B located throughout the leaflet. Lower side: Yellow-Green Group 146C with anthocyanic intonations of Greyed-Purple 183B throughout the leaflet.

Plant leaves and leaflets:

*Stipules.*—Size: 30 mm in length. Shape: Linear, slightly broad based with outward extending apecies. Margins: Serrated with many stipitate glands. Color: Upper surface: Yellow-Green Group 146A. Lower surface: Yellow-Green Group 146B. Anthocyanin: Color: Greyed-Purple Group 183A.

*Petiole.*—Length: 30 mm. Diameter: 2 mm.

*Upper surface: Color: Yellow-Green Group* 146B.

*Lower surface.*—Color: Yellow-Green Group 146C. Observations: Few stipitate glands and few small prickles observed.

*Rachis.*—Length: 60 mm. Upper surface: Color: Yellow-Green Group 146B. Lower surface: Color: Yellow-Green Group 146C. Observations: Few stipitate glands and few small prickles observed.

*Leaflet.*—Edge: Serrated. Size: Average size of the terminal leaflet on normal leaves is 35 mm in length by 25 mm wide. Shape: Generally elliptical to orbicular. Base: Rounded. Apex: Cuspidate. Texture: Rugose. Thickness: Thick. Arrangement: Odd pinnate. Venation: Reticulate. Glossiness: Very glossy.

Disease resistance: Above average resistance to powdery and downy mildews, rust, black spot, and *Botrytis* under normal growing conditions in Jackson County, Oreg.

Cold hardiness: The variety 'Poulcy011' has been found to be cold tolerant to USDA Cold Hardiness Zone 6.

It is claimed:

1. A new and distinct variety of rose plant of the climbing rose class named 'Poulcy011', substantially as illustrated and described herein as a distinct and novel rose variety due to its abundant pink flowers, disease resistance, and extended period of bloom.

* * * * *

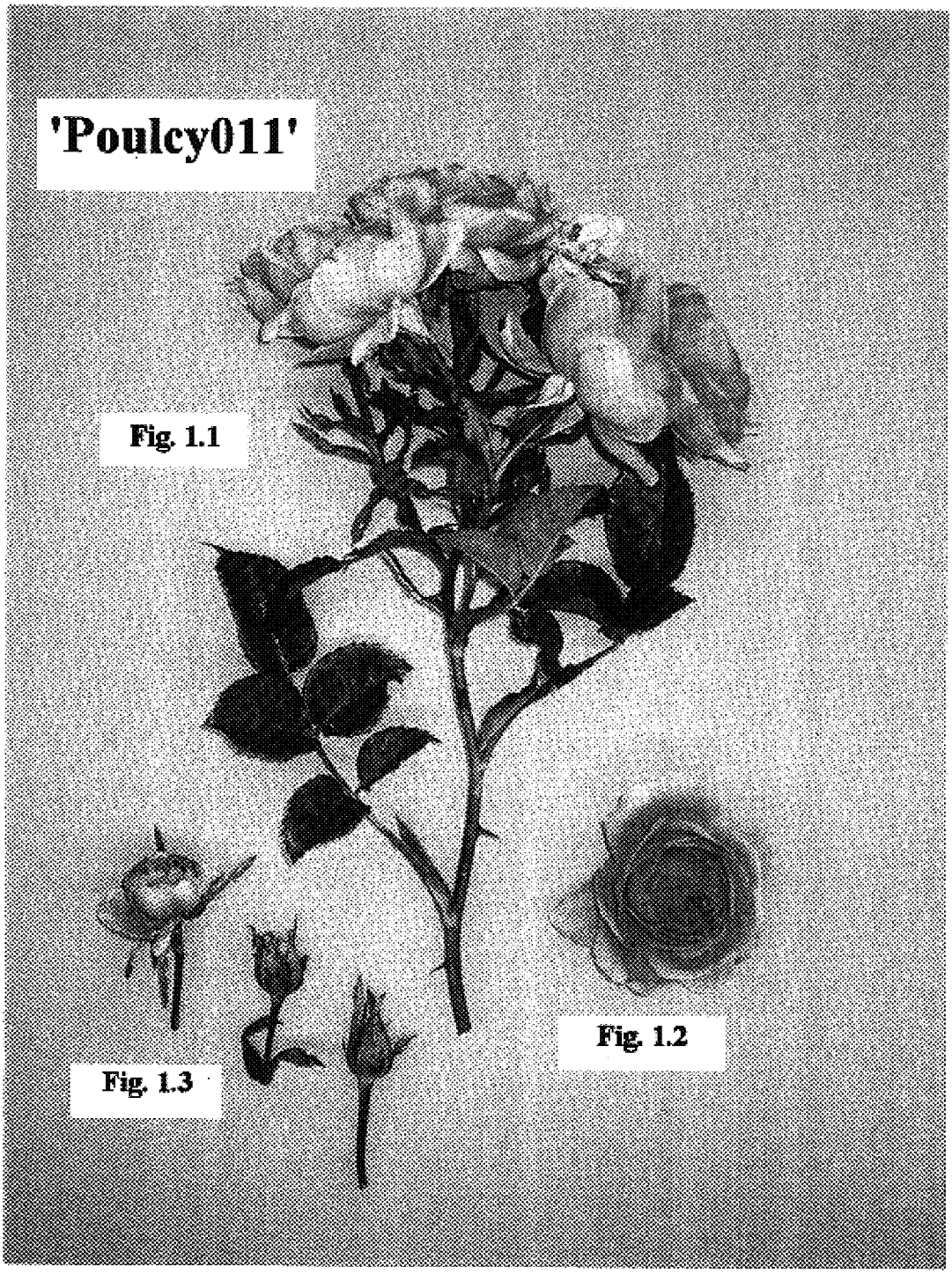
'Poulcy011'
Fig. 1.1
Fig. 1.2
Fig. 1.3

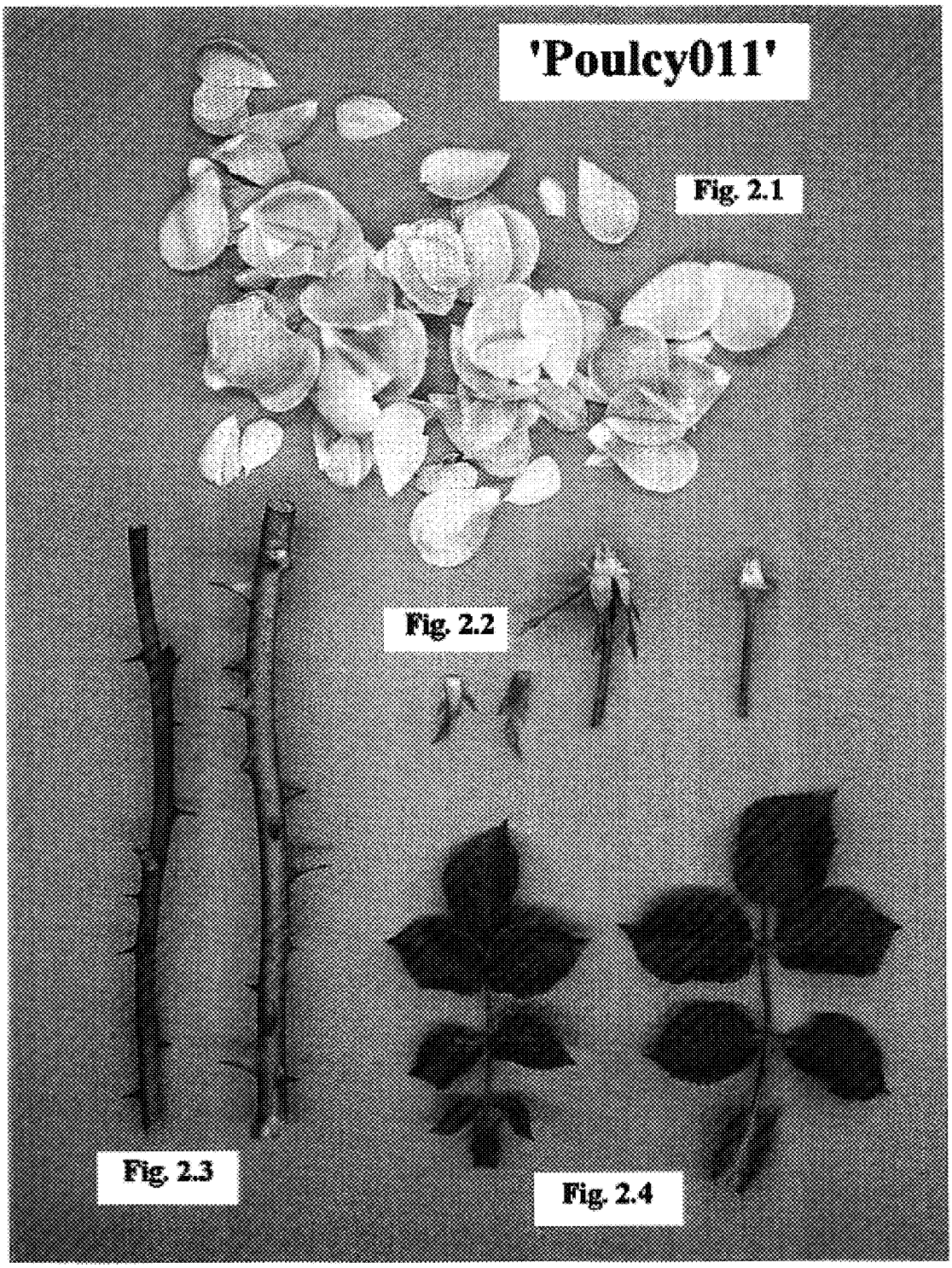
'Poulcy011'
Fig. 2.1
Fig. 2.2
Fig. 2.3
Fig. 2.4